United States Patent [19]
Shimada et al.

[11] Patent Number: 5,443,957
[45] Date of Patent: Aug. 22, 1995

[54] ANTI-ASIALO-GM1 MONOCLONAL ANTIBODIES AND METHOD OF USE

[75] Inventors: Shizio Shimada; Tadashi Sudo; Daiji Iwata, all of Chiba, Japan

[73] Assignee: Mitsui Toatsu Chemicals, Inc., Tokyo, Japan

[21] Appl. No.: 225,075

[22] Filed: Apr. 8, 1994

Related U.S. Application Data

[63] Continuation of Ser. No. 701,564, May 14, 1991, abandoned, which is a continuation of Ser. No. 438,994, Nov. 22, 1989, abandoned, which is a continuation of Ser. No. 888,712, Jul. 24, 1986, abandoned.

[30] Foreign Application Priority Data

Jul. 30, 1985 [JP] Japan ................... 60-166693

[51] Int. Cl.$^6$ ................... G01N 33/53; G01N 33/577; C12N 5/20; C07K 16/28
[52] U.S. Cl. ................... 435/7.24; 435/70.21; 435/172.2; 435/240.27; 436/548; 530/387.5; 530/388.73; 530/388.8; 530/388.85; 530/389.6; 530/389.7
[58] Field of Search ............... 435/7.24, 70.21, 172.2, 435/240.27; 436/548; 530/387.5, 387.7, 388.73, 388.8, 388.85, 389.6, 389.7

[56] References Cited

PUBLICATIONS

Jacquemart et al. (Jacquemart), "Production and Characterization of a mouse Monoclonal Antibody to the Glycolipid Asialo-GM1," *Hybridoma*, vol. 7, No. 4, 1988, pp. 323-331.

Kannagi et al. (Kannagi), "Monoclonal antibodies directed to carbohydrate antigens," Handbook of *Experimental Immunology*, vol. 4, 4th Ed., pp. 117.1-117.20.

Kasai, M. et al. "Aglycolipid on the Surface of Mouse Natural Killer Cells," *Eur. J. Immunol.* 10: 175-180, 1980.

Kuo, M.-C. et al. "Rabbit-Mouse Hybridomas Secreting Intact Rabbit Immunoglobulius," *Molecular Immunology* 22(4): 351-359, 1985.

Chemical Abstracts, vol. 92, No. 5, 4th Feb. 1980, p. 591, abstract No. 39574q, Columbus, Ohio.

Society For Neuroscience Abstracts, Bol. 10, No. 1, 1984, p. 82, New York, U.S.

Molecular Immunology, vol. 22, No. 11, Nov. 1985, pp. 1265-1271, Pergamon Press Ltd., GB.

Pereira et al, "Immunochemical Studies on the Specificity of the Peanut (Arachis hypogaea) Agglutinin", *Carbohydrate Research*, 51, (1976) pp. 107-118.

Higashi et al. "Sensitive Enzyme-Immunostaining and Densitometric Determination on Thin-Layer Chromatography of N-Glycolylneuraminic Acid-Containing Glycosphingolipids, Hanganutziu-Deicher Antigens", *J. Biochem* 95, 1517-1520 (1984).

Uchida et al, "Affinity Chromatographic Purification of Anti-Glycolipid Antibodies and Their Application to the Membrane Studies", *J. Biochem.* 87 1829-1841 (1980).

Young et al, "Production of Monoclonal Antibodies Specific for Two Distinct Steric Portions of the Glycolipid Ganglio-N-Triocylceramide (Asialo GM$_2$)" *J. Exp. Med.*, 150, 1008-1018 (1979).

Köhler et al, "Continuous Cultures of Fused Cells Secreting Antibody of Predefined Specificity", *Nature*, 256, 495-497 (1975).

Sanai et al, "Enzyme-Linked Immunosorbent Assay (Elisa) for Detection of Antibodies against Glycosphingolipids and Its Application to Patients with Systemic Lupus Erythematosus", *Japan. J. Exp. Med.*, 51, 309-316, (1981).

Taki et al, "Determination of Glycolipid in Sera from Cancer Patients by Elisa Method and its Application to Cancer Diagnosis", *Proceedings of the Japanese Cancer Association*, 1984, p. 418.

*Primary Examiner*—Robert D. Budens
*Attorney, Agent, or Firm*—Browdy and Neimark

[57] ABSTRACT

A monoclonal antibody which reacts with glycolipid asialo GM1 but not with any of glycolipids GM1 and GM2 can be produced by hybridoma cells obtained by fusing antibody-producing cells of a mammal immunized with the glycolipid asialo GM1 with myeloma cells.

3 Claims, 1 Drawing Sheet

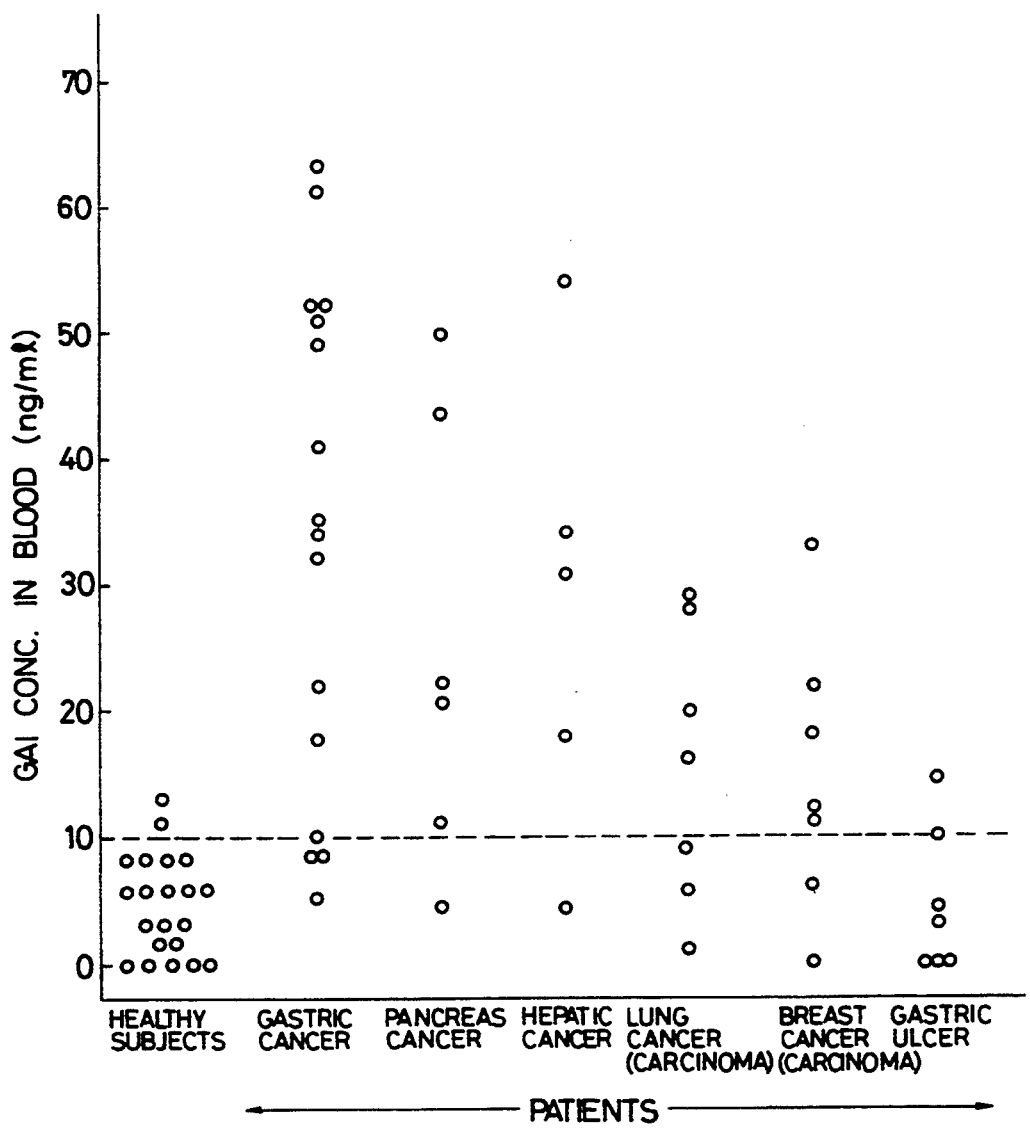

ANTI-ASIALO-GM1 MONOCLONAL ANTIBODIES AND METHOD OF USE

This application is a continuation of application Ser. No. 07/701,564, filed May 14, 1991, now abandoned, which is a continuation of application Ser. No. 07/438,994, filed Nov. 22, 1989, now abandoned, which is a continuation of application Ser. No. 06/888,712, filed Jul. 24, 1986, now abandoned.

FIELD OF THE INVENTION

This invention relates to a novel monoclonal antibody which specifically reacts with glycolipid asialo GM1 (referred to briefly as GA1).

BACKGROUND OF THE INVENTION

In the present specification, sugars, lipids and binding manners thereof will be described in such a manner as generally or commonly employed in the art.

Glycolipids have attracted public attention in particular in the field of differentiation and carcinogenesis of cells. In the studies on glycolipids, not only conventional biochemical processes but also immunochemical processes with the use of an antibody specific to each glycolipid have been frequently employed in identifying, determining and purifying the same. Since the techniques for the preparation of monoclonal antibodies developed by Köhler and Milstein have been generalized, it is essential to use monoclonal antibodies in studying glycolipids. However there are many glycolipids commonly observed in animals which are usually used in various experiments. In these cases, immunization among these animals can not bring about the development of any antibody in the blood, which makes the preparation of monoclonal antibodies impossible.

Further, even if immunization can be established in an animal, it is difficult to prepare a monoclonal antibody if antibody-producing cells, which will be also referred to as immunocytes hereinafter, of said animal can not play a satisfactory role as a partner of myeloma cells conventionally used in the preparation of hybridoma cells. Glycolipid GA1 is an example thereof. Namely, GA1 is present in the tissues and on the cell surfaces of a mouse, a rat and a normal man but absent in a rabbit. Therefore an antibody against GA1 is normally obtained by immunizing a rabbit. However it is frequently observed that antibody-producing cells of a rabbit can not be a desirable partner of myeloma cells of a mouse or a rat. Thus there has been no report of success in the preparation of a monoclonal antibody against GA1.

We have studied in order to prepare an antibody against a substance which is present in a mouse, a rat and a man in a normal state, i.e., a constituent per se. As a result, we have succeeded in the preparation of a monoclonal antibody agaisnt GA1, which is a constituent of a rat and a man, by selecting an animal which exhibits a relatively high immune response to a material of a low immunogenicity, thus completing the present invention.

Further we have assayed GA1 concentration in the sera of human patients suffering from cancer with the use of a monoclonal antibodies against said GA1 and consequently found that the GA1 concentration in the blood of a cancer patient is higher than those of normal men or those suffering from benign diseases regardless of the type of cancer.

Taki et al. have reported on the diagnosis of cancer through the assay of the GA1 concentration in blood with the use of anti-GA1 antibody (cf. 43rd Proceedings of the Japanese Cancer Association, p. 418 (1984)). In the above report, they used a polyclonal anti-GA1 antibody purified from an antiserum obtained by immunizing a rabbit with GA1.

It is believed that a method for detecting a glycolipid with the use of a polyclonal antibody thereto is not completely reliable in its accuracy when compared with the one wherein a monoclonal antibody is used. Therefore the diagnosis of cancer with the use of the monoclonal anti-GA1 antibody of the present invention is superior.

Thus the monoclonal anti-GA1 antibody of the present invention is highly useful not only in the basic studies on glycolipids but in the diagnosis of cancer.

SUMMARY OF THE INVENTION

The monoclonal anti-GA1 antibody of the present invention is prepared by fusing antibody-producing cells of a mammal immunized with glycolipid GA1 with myeloma cells to a mammal immunized with glycolipid GA1 with myeloma cells to thereby form hybridoma cells and isolating a monoclonal antibody having the abovementioned properties therefrom.

BRIEF DESCRIPTION OF THE DRAWING

FIG. 1 shows the concentrations of GA1 (ng/ml) determined by ELISA method in the blood samples collected from patients suffering from various types of cancer.

DETAILED DESCRIPTION OF THE INVENTION

In the present invention, the preparation of the hybridoma cells may be carried out according to a known method, for example, the one described in Nature, 256, 495 (1975) and variations thereof (cf. J. Expt. Med., 150., 1008 (1979)).

As the immunogen, GA1 purified from the bovine brain or cells of various mammals having the same on the surface may be used.

The mammal to be immunized with GA1 is not strictly limited. It is preferable to select said animal by considering the suitability to the myeloma cells to be used in cell fusion. Man, mouse and rat are generally used although rabbit or other animals may be used in some cases.

Furthermore model animals of autoimmune diseases such as NBZ, NZW or NZB/WF1 mice may be used if required.

The immunization with GA1 may be carried out either in vitro or in vivo. When it is carried out in vivo, GA1 may be diluted with, for example, a physiological saline or a phosphate-buffered saline (PBS) to give an appropriate concentration and intravenously, subcutaneously or intraperitoneally administered to an animal. More particuarly, it is preferable that purified GA1 is appropriately diluted with, for example, PBS and administered to an animal simultaneously with conventional carriers such as *Salmonella minnesota* or bovine serum albumin, which will be abbreviated as BSA hereinafter, several times at an interval of four to 14 days to give a total dose of 10 to 100 μg per individual. An immunization in vivo with the use of membrane components or cells per se may be carried out in a similar manner as the one described above. For example, membrane components may be administered in a total dose of 1 to 100 mg per individual while cells per se may be administered in a total dose of $10^6$ to $10^8$ per individual. The antibody-producing cells used in the immunization in vivo may be spleen cells, lymph node cells, peritoneal lymphocytes or peripheral blood lymphocytes. It is most preferable to use spleen cells approximately four days after the final immunization.

The immunization in vitro may be carried out via a so-called sensitization in vitro. Namely, lymphocytes selected from among spleen cells, lymph node cells, peritoneal lymphocytes and peripheral blood lymphocytes are incubated with GA1, which serves as the antigen, for one week to thereby develop the cells producing the antibody against GA1 In this case, purified GA1 may be dissolved in a medium for cell incubation or adsorbed on an appropriate carrier such as sheep erythrocytes, liposome or *Salmonella minnesota* followed by incubating with lymphocytes. When using cells per se or its membrane components containing GA1 as the immunogen, they may be dissolved or suspended in a medium and incubated with lymphocytes. When employing the cells per se, it is preferable to treat the same with mitomycin or to irradiate the same prior to the incubation with lymphocytes.

Any medium conventionally used in incubating lymphocytes, for example, RPMI 1640 or Dulbecco's MEM media may be employed in the incubation of the lymphocytes. It is desirable to add fetal calf serum, which will be abbreviated as FCS hereinafter, thereto at a concentration of 5 to 20% at the use. Further the medium may contain 2-mercaptoethanol and pokeweed mitogen, which will be abbreviated as PWM hereinafter, at concentration of $5 \times 10^{-5}$M and 5 to 30 µg/ml, respectively if required to thereby efficiently sensitize GA1 in vitro.

The cell concentration of the lymphocytes varies depending on the device to be used in the incubation. It is generally desirable to adjust the same within a range of $10^6$ to $10^7$/ml.

It is desirable to employ the purified GA1, GA1-containing cells and membrane components thereof, which serve as the immunogens, at concentrations of 1 to 20 µg/ml, 1 to 100 mg/ml and 0.1 to 10 mg/ml, respectively.

Then the antibody-producing cells obtained by immunizing either in vivo or in vitro as described above are fused with myeloma cells.

As the myeloma cells, various known ones such as NS-1, P3, P3-U1, X45, X63.6.5.3 and SP2 of a mouse and Ys.Ag1.2.3 of a rat may be employed. The cell fusion may be carried out according to a known method, for example, by incubating in a medium containing fusogens.

Examples of the fusogens are polyethylene glycol, which will be abbreviated as PEG hereinafter, and Sendai virus. Furthermore adjuvants such as dimethyl sulfoxide may be used to thereby enhance the fusion efficiency.

The immunocytes and the myeloma cells may be used in the same proportion as those employed in conventional methods. For example, the former may be used in an amount of approximately one to ten times as much as the latter.

Any conventional medium used in cell incubation may be used in the fusion. It is usually desirable to remove sera such as FCS therefrom.

The fusion may be carried out by thoroughly mixing the above immunocytes with the myeloma cells in the medium as defined above, centrifuging the same, separating the supernatant and adding a solution of PEG having an average molecular weight of 1,000 to 6,000 previously heated to approximately 37° C. to a conventional medium at a concentration of approximately 30 to 60 w/v % followed by mixing therewith. Subsequently the procedure of adding an appropriate media thereto, centrifuging the mixture and separating the supernatant may be successively repeated to thereby form the hybridoma cells.

The aimed hybridoma cells may be isolated by incubating the cells after the cell fusion in a medium conventionally used in selecting hybridoma cells. The above-mentioned myeloma cell strain is hypoxanthin-guanine-phosphoribosyl transferase deficient. Thus it can not grow in a HAT medium comprising hypoxanthine, aminopterine and thymidine. Therefore the cells growing in the HAT medium may be selected. The cell incubation in said HAT medium may be carried out for a sufficient period until the cells other than the aimed hybridoma cells die out, usually for several days to several weeks.

The hybridoma cells thus obtained may be subjected to a conventional limiting dilution method to thereby detect the aimed antibody-producing cells and monoclonalization of the same.

Said antibody-producing cells may be detected by various methods generally used in detecting antibodies, such as enzyme-linked immunosorbent assay (ELISA) method (cf. Jpn. J. Expt. Med., 51, 309 (1981)), plaque method, spot method, agglutination method, Ouchterlony method and radioimmunoassay (RIA).

More particularly, a plastic plate coated with purified GA1 is reacted with the supernatant obtained from the incubation of specimen hybridoma cells and the presence of the antibody bound to the corresponding purified glycolipid is confirmed by a conventional manner, for example, through a peroxidase reaction with the use of peroxidase-conjugated antibody against mouse immunoglobulins when the immunocytes are those derived from a mouse, to thereby select the aimed antibody-producing cells.

The hybridoma cells producing the monoclonal antibody of the present invention thus obtained can be subcultured in a conventional medium and readily preserved in liquid nitrogen for a prolonged period of time.

The hybridoma MW-1 prepared in the Example 1 as will be described below has been deposited with IFO (Institute for Fermentation, Osaka) as No. IFO 50091.

The monoclonal antibody of the present invention may be obtained from the particular hybridoma cells as obtained above by incubating said hybridoma cells in a conventional manner and isolating the aimed antibody from the supernatant or administering said hybridoma cells to a mammal suitable therefor and isolating the aimed antibody from its serum or ascitic fluid.

As will be described below, the monoclonal antibody of the present invention thus obtained specifically recognizes GA1 appearing in the serum of a human patient suffering from cancer. Therefore it is extremely useful in the diagnosis, treatment and studies on human cancer.

To further illustrate the present invention, the following Examples will be given.

EXAMPLE 1

100 µg of purified GA1 and 400 µg of formalinized Salmonella minnesota strain (ATCC No. 9700) were added to 4 ml of a physiological saline maintained at 40° C. and thoroughly stirred to give a homogeneous suspension. The obtained suspension was intravenously administered to a mouse once four days in a unit dose of 10 µg of the GA1 four times in total. Four days after the final administration, the spleen was taken out and $3 \times 10^8$ spleen cells were fused with $3 \times 10^7$ NS-1 myeloma cells (ATCC No. TIB18) in the presence of 50% PEG. The hybridoma cells thus obtained were pipetted into 96-well flat-bottomed plastic plates and incubated in a Dulbecco's MEM medium containing a HAT medium to which 10% of FCS was added under in an atmosphere of 5% carbon dioxide gas at 37° C. The presence of the anti-GA1 antibody was determined in the supernatants of the wells, in which the growth of the hybridoma cells was observed, by the following ELISA method. 0.05-ml portions of a GA1 solution in ethyl alcohol (10µg/ml) were pipetted into the wells of each 96-well plastic plate and the solvent was allowed to evaporate. Thus the GA1 was adsorbed by the plate. The test incubation supernatant employed as the primary antibody was reacted in each well. After thoroughly washing, peroxidase-conjugated antibody against mouse immnoglobulins employed as the secondary antibody was reacted therein.

Subsequently a peroxidase reaction with the use of o-phenylenediamine as the substrate was performed. Then the extent of color development of each well was observed by the naked eye or with a 96-well ELISA autoreader at 490 nm.

The hybridoma cells in the wells wherein anti-GA1 antibody titer was observed in the supernatant were further subjected to cloning by the limiting dilution method to thereby give monoclones.

The monoclonal hybridoma cells thus obtained were grown in a plastic flask for incubation and intraperitoneally transplanted into a BALB/c nude mouse which was previously treated with an immunodepressing agent, pristane (2,6,10,14-tetramethylpentadecane, mfd. by Aldrich Chemical Co., Inc.).

Then the monoclonal antibodies were purified from the obtained ascitic fluid by a 50%-saturated ammonium sulfate precipitation method.

Thus the monoclonal anti-GA1 antibodies could be obtained from the tested animal. In the Test Examples which will be described below, four clones obtained herein, i.e., Nos. MW-1, MW-2, MW-3 and MW-4 were employed.

EXAMPLE 2

2 mg of purified GA1 and 1 mg of BSA were suspended or dissolved in 1 ml of a physiological saline. Then a water-in-oil emulsion was formed by using the same volume of a Freund's complete adjuvant. 0.2-ml portions of the obtained emulsion were injected into the foot pads of four limbs of a New Zealand white rabbit. Four weeks thereafter, an emulsion containing GA1 was prepared in the same manner as the one used in the first immunization and 1 ml of the same was subcutaneously injected into the dorsum of the animal for booster. Four days thereafter, the spleen of the animal was taken out and fused with myeloma cells NS-1 followed by cloning in the same manner as the one described in Example 1 to give monoclonal antibodies. After the cell fusion, the hybridoma cells were grown in a HAT medium with the use of a 24-well plastic plate. Peroxidase-conjugated antibody against rabbit immunoglobulines globulines was employed as the secondary antibody in the ELISA method.

EXAMPLE 3

Mononuclear lymphocytes were prepared from human peripheral blood in a conventional manner with the use of Ficoll-Paque (mfd. by Pharmacia AB) and suspended at a concentration of $1 \times 10^7$ /ml.

To an RPMI 1640 medium containing 10% of FCS, 2-mercaptoethanol and PWM were further added to give concentrations of $5 \times 10^{-5}$ M and 30 µg/ml, respectively, at the use.

Subsequently 1 ml of the lymphocyte suspension ($1 \times 10^7$ /ml) and 10 ml of a medium free from PWM were respectively introduced into the inner and outer vessels of a Marbrook-type culture bottle and a dialyzing membrane was provided at the interface of the inner and outer liquors.

GA1 was incorporated into liposomes consisting of egg yolk lecithine and cholesterol, prepared according to the method reported by Uchida et al. (cf. J. Biochem., 87, 1829 (1980)), and added to the inner vessel of the culture bottle at a GA1 concentration of 5 µg/ml.

Thus the lymphocytes were incubated together with the GA1 in an atmosphere of 5% carbon dioxide gas at 37° C. for six days. Subsequently the cell fusion with NS-1 and cloning were carried out in the same manner as the one described in Example 1 to thereby give monoclonal antibodies.

In this Example, peroxidase-conjugated antibody against human immunoglobulins was employed as the secondary antibody in the ELISA method.

Test Example 1

Immunoglobulin class

The immunoglobulin classes of the monoclonal anti-GA1 antibodies MW-1, MW-2, MW-3 and MW-4 as obtained in Example 1 were determined by the ELISA method. Namely, each monoclonal anti-GA1 antibody, serving as the antigen, was reacted with an antibody against each class of peroxidase-conjugated mouse immunoglobulins. Then the color development by an enzymatic reaction of the peroxidase with the use of o-phenylenediamine as the substrate was performed.

Consequently it was found that all of MW-1, MW-2, MW-3 and MW-4 belonged to IgM.

Test Example 2

The antibody titers of MW-1, MW-2, MW-3 and MW-4 as obtained in Example 1 on GlcCer, LacCer, Gb3, Gb4, GA2, GM3, GM2, GM1, GD1a and GD1b each having a similar structure to that of GA1 were examined according to the ELISA method as described in Example 1. The antibody titer of each anti-GA1 antibody on each glycolipid was represented by the maximum dilution ratio in terms of the involution of 2 at which the coloration could be observed with the naked eye.

As a result, MW-1, MW-2, MW-3 and MW-4 showed each a high antibody titer on GA1 ($2^{16}$ to $2^{18}$). However none of these antibodies reacted with the other glycolipids, i.e. every antibody titer thereon was 24 or below.

Test Example 3

It has been known that polyclonal anti-GA1 antibodies obtained by immunizing a rabbit can damage mouse natural killer cells, which will be abbreviated as NK cells hereinafter, in the presence of a complement (cf. Eur. J. Immun., 10, 175 (1980)).

Thus we examined whether the monoclonal anti-GA1 antibodies of the present invention could exhibit a similar effect or not.

Spleen cells of a C57BL/6 mouse were suspended in a ten-fold dilution of MW-1, MW-2, MW-3 or MW-4 and the obtained suspension was allowed to stand at 4° C. for 30 minutes. Then the spleen cells were thoroughly washed, suspended in guinea pig serum employed as a complement and maintained at 37° C. for 40 minutes. $5 \times 10^5$ viable spleen cells thus obtained and $1 \times 10^4$ YAC-1 lymphoma cells labeled with $^{51}Cr$ were added to 0.2 ml of an RPMI 1640 medium containing 10% of FCS and maintained at 37° C. in an atmosphere of 5% carbon dioxide gas. Four hours thereafter, 0.1 ml of the supernatant was collected and the radioactivity of the $^{51}Cr$ contained therein was determined with a gamma counter.

The NK activity was calculated in a conventional manner according to the following equation, wherein the spontaneous release count and the maximum release count respectively represent the count obtained by using the YAC-1 cells alone and that obtained in the presence of 10 0.5N hydrochloric acid.

$$NK\ activity\ (\%) = \frac{\left(\begin{array}{c}\text{count of}\\ \text{test group}\end{array}\right) - \left(\begin{array}{c}\text{spontaneous}\\ \text{release count}\end{array}\right)}{\left(\begin{array}{c}\text{maximum}\\ \text{release count}\end{array}\right) - \left(\begin{array}{c}\text{spontaneous}\\ \text{release count}\end{array}\right)} \times 100$$

As shown in the following Table 2, every monoclonal antibody damaged mouse NK cells similar to the rabbit polyclonal antibodies. This result also suggests that MW-1, MW-2, MW-3 and MW-4 are antibodies specific to GA1.

TABLE 2

| Treatment on spleen cells | NK activity % | relative value* |
|---|---|---|
| Untreated | 42.7 | 102 |
| Complement alone | 43.6 | 100 |
| MW-1 + complement | 27.2 | 62 |
| MW-2 + complement | 32.8 | 75 |
| MW-3 + complement | 16.4 | 38 |
| MW-4 + complement | 21.4 | 49 |
| Normal mouse serum + complement | 43.1 | 99 |
| Rabbit anti-GA1 antibody + complement | 3.0 | 7 |

*: The value of the group treated with the complement alone is referred to as 100.

Test Example 4

The epitope specificity of MW-1, MW-2, MW-3 or MW-4 each obtained in Example 1 was examined by enzymeimmunostaining of glycolipids fractionated by thin layer chromatography.

Various purified glycolipids including GA1 were spotted on silica gel thin layer plates (Polygram Sil G; mfd. by Macherei-Nagel) according to the method of Matsumoto et al. (cf. J. Biochem., 95, 1517 (1984)). Then each plate was developed with the use of chloroform/methanol/0.25% potassium chloride (50: 40: 10 by volume) as a solvent for approximately 25 minutes. After the development, the position of the spot of each glycolipid was determined through the Orcinol reaction.

Thin layer chromatography-for enzyme-immunostaining was carried out in the following manner simultaneously with the Orcinol reaction. Namely, MW-1, MW-2, MW-3 or MW-4, each employed as a primary antibody, was reacted with each developed thin layer plate and then peroxidaseconjugated antibody against mouse immunoglobulins, i.e. the secondary antibody, was further reacted therewith. 4-Chloro-1-naphthol was used as the substrate for the peroxidase and each spot was subjected to color development through the enzymatic reaction.

In addition, peanut agglutin, which is known to specifically recognize Gal-3GalNAc and will be abbreviated as PNA hereinafter, was employed as a reference (cf. Carbohydrate Research, 51, 107 (1976)). In this case, peroxidase-conjugated antibody against PNA was used as the secondary antibody.

As shown in Table 3, each glycolipid employed in this test showed a characteristic Rf value. The result of the enzyme-immunostaining suggests that all of MW-1, MW-2, MW-3 and MW-4 reacted with the spot corresponding to GA1 alone. On the other hand, PNA reacted with the spots corresponding to GA1 and GM1.

TABLE 3

| Glycolipid | Rf value | Enzyme-staining* | | | | |
|---|---|---|---|---|---|---|
| | | MW-1 | MW-2 | MW-3 | MW-4 | PNA |
| GlcCer | 0.74 | − | − | − | − | − |
| LacCer | 0.64 | − | − | − | − | − |
| GA$_2$ | 0.60 | − | − | − | − | − |
| crude GA$_1$ | 0.56 | + | + | + | + | − |
| GA$_1$ | 0.40 | + | + | + | + | + |
| GM$_3$ | 0.36 | − | − | − | − | − |
| GM$_2$ | 0.29 | − | − | − | − | − |
| GM$_1$ | 0.23 | − | − | − | − | + |
| GD$_{1a}$ | 0.16 | − | − | − | − | − |
| GD$_{1b}$ | 0.14 | − | − | − | − | − |
| Gb$_3$ | 0.53 | − | − | − | − | − |
| Gb$_4$ | 0.47 | − | − | − | − | − |

*− represent negative color development while + represents positive color development.

These results suggest that any of the monoclonal anti-GA1 antibodies of the four clones as prepared in Example 1, i.e., MW-1, MW-2, MW-3 and MW-4 might recognize the structure of Gal$\beta$1→3GalNac$\beta$1→4Gal$\beta$1→4Glc or Gal$\beta$1→3GalNAc$\beta$1→4Gal.

Test Example 5

Assay of GA1 in blood of patients of cancer

The concentrations of GA1 in the blood samples obtained from patients suffering from cancer were assayed by the ELISA method with the use of MW-1 obtained in Example 1.

MW-1 was appropriately diluted and mixed with each test serum. The obtained mixture was allowed to stand at room temperature for two hours. Then polystyrene 10 balls on which GA1 was adsorbed were added to the mixture and maintained at 37° C. for four hours. Then the balls were thoroughly washed and an appropriately diluted solution of peroxidase-conjugated rabbit polyclonal antibody against mouse immunoglobulin was added thereto. The resulting mixture was allowed to react at 4° C. overnight. Subsequently an enzymatic reaction was carried out with the use of o-phenylenediamine as the substrate and the color development thus brought about was determined at 490 nm.

A standard curve was formed with the use of the sera of healthy subjects thoroughly absorbing GA1 by using rabbit anti-GA1 antibody and containing a required concentration of GA1. The GA1 concentration of each test serum was determined therefrom.

FIG. 1 shows the result. Patients suffering from cancer showed higher GA1 concentrations in blood regardless of the type of the cancer, than that of the healthy subjects (ca. 10 ng/ml). Accordingly, the monoclonal anti-GA1 antibodies of the present invention are highly useful in the diagnosis of cancer.

TABLE 4

| Glycolipid | Structure |
| --- | --- |
| GlcCer | Glc$\beta$1→1Cer |
| LacCer | Gal$\beta$1→4Glc$\beta$1→1Cer |
| Gb$_3$ | Gal$\alpha$1→4Gal$\beta$1→4Glc$\beta$1→1Cer |
| Gb$_4$ | GalNAc$\beta$1→3Gal$\alpha$1→4Gal$\beta$1→4Glc$\beta$1→1Cer |
| GA$_2$ | GalNAc$\beta$1→4Gal$\beta$1→4Glc$\beta$1→1Cer |
| GA$_1$ | Gal$\beta$1→3GalNAC$\beta$1→4Gal$\beta$1→4Glc$\beta$1→1Cer |
| GM$_3$ | SA$\alpha$2→3Gal$\beta$1→4Glc$\beta$1→1Cer |
| GM$_2$ | GalNAc$\beta$1→4[SA$\alpha$2→3]Gal$\beta$1→4Glc$\beta$1→1Cer |
| GM$_1$ | Gal$\beta$1→3GalNAc$\beta$1→4[SA$\alpha$2→3]Gal$\beta$1→4Glc$\beta$1→1Cer |
| GD$_{1a}$ | SA$\alpha$2→3Gal$\beta$1→3GalNAc$\beta$1→4[SA$\alpha$2→3]Gal$\beta$1→4Glc$\beta$1→1Cer |
| GD$_{1b}$ | Gal$\beta$1→3GalNAc$\beta$1→4[SA$\alpha$2→8SA$\alpha$2→3]Gal$\beta$1→4Glc$\beta$1→1Cer |

*In the above Table, Glc, Gal, GalNAC, SA and Cer represent glucose, galactose, N-acetylgalactosamine, sialic acid and ceramide, repectively.

What is claimed is:

1. A hybridoma selected from the group consisting of hybridoma cell line MW-1 FERM BP-2412, MW-2 FERM BP-2413, and MW-3 FERM BP-2414.

2. A monoclonal anti-asialo GM1 antibody which binds specifically to glycolipid asialo GM1 but does not bind specifically to any of GlcCer, LacCer, Gb3, Gb4, GA2, GM2, GM3, GM1, GD1a and GD1b, and is produced by a hybridoma cell line selected from the group consisting of MW-1 FERM BP-2412, MW-2 FERM BP-2413, and MW-3 FERM BP-2414.

3. In an immunological method for assaying of asialo GM1 concentration in blood, the improvement comprising using as antibody the monoclonal anti-asialo GM1 antibody of claim 2.

* * * * *